(12) United States Patent
Jiang et al.

(10) Patent No.: US 11,122,836 B2
(45) Date of Patent: Sep. 21, 2021

(54) ATOMIZER AND ELECTRONIC CIGARETTE HAVING SAME

(71) Applicant: Shenzhen First Union Technology Co., Ltd., Shenzhen (CN)

(72) Inventors: Zhanjun Jiang, Shenzhen (CN); Yonglu Guo, Shenzhen (CN); Yonghai Li, Shenzhen (CN); Zhongli Xu, Shenzhen (CN)

(73) Assignee: Shenzhen First Union Technology Co., Ltd., Shenzhen (CN)

( * ) Notice: Subject to any disclaimer, the term of this patent is extended or adjusted under 35 U.S.C. 154(b) by 532 days.

(21) Appl. No.: 15/939,396

(22) Filed: Mar. 29, 2018

(65) Prior Publication Data
US 2018/0280636 A1 Oct. 4, 2018

(30) Foreign Application Priority Data
Mar. 31, 2017 (CN) .......................... 201720334848.7

(51) Int. Cl.
| | |
|---|---|
| *A24F 40/46* | (2020.01) |
| *A24F 40/44* | (2020.01) |
| *A24F 40/485* | (2020.01) |
| *A61M 11/04* | (2006.01) |
| *A61M 15/00* | (2006.01) |
| *A61M 15/06* | (2006.01) |
| *A24F 40/10* | (2020.01) |

(52) U.S. Cl.
CPC ............. *A24F 40/46* (2020.01); *A24F 40/44* (2020.01); *A24F 40/485* (2020.01); *A61M 11/042* (2014.02); *A61M 15/002* (2014.02); *A61M 15/06* (2013.01); *A24F 40/10* (2020.01)

(58) Field of Classification Search
None
See application file for complete search history.

(56) References Cited

U.S. PATENT DOCUMENTS
2014/0353856 A1  12/2014  Dubief

FOREIGN PATENT DOCUMENTS
| | | |
|---|---|---|
| CN | 204 032 373 U | 12/2014 |
| WO | 2015/062136 A1 | 5/2015 |

*Primary Examiner* — Phu H Nguyen
(74) *Attorney, Agent, or Firm* — PROI Intellectual Property US; Klaus Michael Schmid

(57) ABSTRACT

An atomizer with adjustable air intake quantity is disclosed including: an atomizer body, having a liquid storage chamber formed therein for storing tobacco liquid; an aerosol generator, configured for aerosolizing the tobacco liquid from the liquid storage chamber to generate an aerosol; at least one air inlet, formed on the atomizer body; an air pipe, disposed inside of the atomizer body and configured for conducting the aerosol to flow along the air pipe; the air inlet being in communication with the air pipe; and an adjusting cover, connected with the atomizer body by a thread to cover the air inlet; the adjusting cover is configured for being rotated to move up and down along axial direction of the atomizer body, to adjust a clearance between an edge of the adjusting cover and the atomizer body.

11 Claims, 6 Drawing Sheets

ATOMIZER AND ELECTRONIC CIGARETTE HAVING SAME

TECHNICAL FIELD

The present disclosure relates to the field of electronic cigarette sets, and in particular, to an atomizer with adjustable air intake quantity, and an electronic cigarette having same.

BACKGROUND ART

Currently, in the market, a typical electronic cigarette has a function of adjusting air intake quantity, by which, concentration of an aerosol generated by the atomizer is changed, allowing the users to achieve different taste flavors. In the prior art, the technical schemes of adjusting air intake quantity are realized by a rotating ring with a side opening to permit a stepless adjustment of the air intake quantity in a 360-degree view. That is, by changing an overlapping area between the side opening on the rotating ring and the air inlet, with a positioning pillar to limit the position, the air intake quantity is changed. However, the cost for designing the structure is pretty high, so is the cost for manually assembling. The air inlet is exposed to exterior of the atomizer, the appearance is not beautiful and the efficiency of assembling is low.

SUMMARY

The present disclosure relates essentially to an atomizer with adjustable air inlet quantity and an electronic cigarette having same, in which the air inlet is concealed not to influence the artistic appearance and the design cost is pretty low.

To overcome the above drawbacks, according to embodiments of the present disclosure, an atomizer with adjustable air inlet quantity including: an atomizer body, having a liquid storage chamber formed therein for storing tobacco liquid; an aerosol generator, configured for aerosolizing the tobacco liquid from the liquid storage chamber to generate an aerosol; at least one air inlet, formed on the atomizer body; an air pipe, disposed inside of the atomizer body and configured for conducting the aerosol to flow along the air pipe; the air inlet being in communication with the air pipe; and an adjusting cover, connected with the atomizer body by a thread to cover the air inlet; the adjusting cover is configured for being rotated to move up and down along axial direction of the atomizer body, to adjust a clearance between an edge of the adjusting cover and the atomizer body.

Furthermore, the atomizer body includes an end cover disposed one end thereof and a base connected with the end cover; the adjusting cover is sleeved on the base and connected with the base by a thread.

Furthermore, at least one air inlet are opened on a lateral wall of the base or the end cover, and evenly spaced.

Furthermore, the end cover has a circular stair, the edge of the adjusting cover abuts against the circular stair, when the adjusting cover is moving up and down, between the edge of the adjusting cover and the stair defines a clearance that allows air to flow into the air inlet.

Furthermore, the end cover has a cylindrical surface, between the cylindrical surface and an inside wall of the adjusting cover defines a wedge-shaped air pipe.

Furthermore, the base has a flange, the adjusting cover includes an ancillary component with a L-shaped section, connected with the flange by a thread; the ancillary component includes a limit tongue, confined between a bottom surface of the flange and a top of the end cover.

Furthermore, a top surface of the flange defines a mounting hole, an elastic element is disposed inside the mounting hole, configured for abutting against top of inner surface of the adjusting cover.

An electronic cigarette is further disclosed, including the atomizer with adjustable air inlet quantity and a power supply, the aerosol generator includes a heating element, the power supply is configured for supplying power to the heating element.

According to some embodiments of the present disclosure, the heating element is a spiral heating wire or a heating tube with several pierced holes opened on a wall of the heating tube.

Compared to the existing technologies known to the inventors, since the atomizer in the present disclosure realizes adjustment of the air inlet quantity by means of an adjusting cover, whereby the structure is simple and the cost of designing is reduced with a simple operation to improve the production efficiency. Since the adjusting cover is engaged with the appearance of the atomizer and conceals the air inlet, the artistic appearance of the electronic cigarette is improved.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
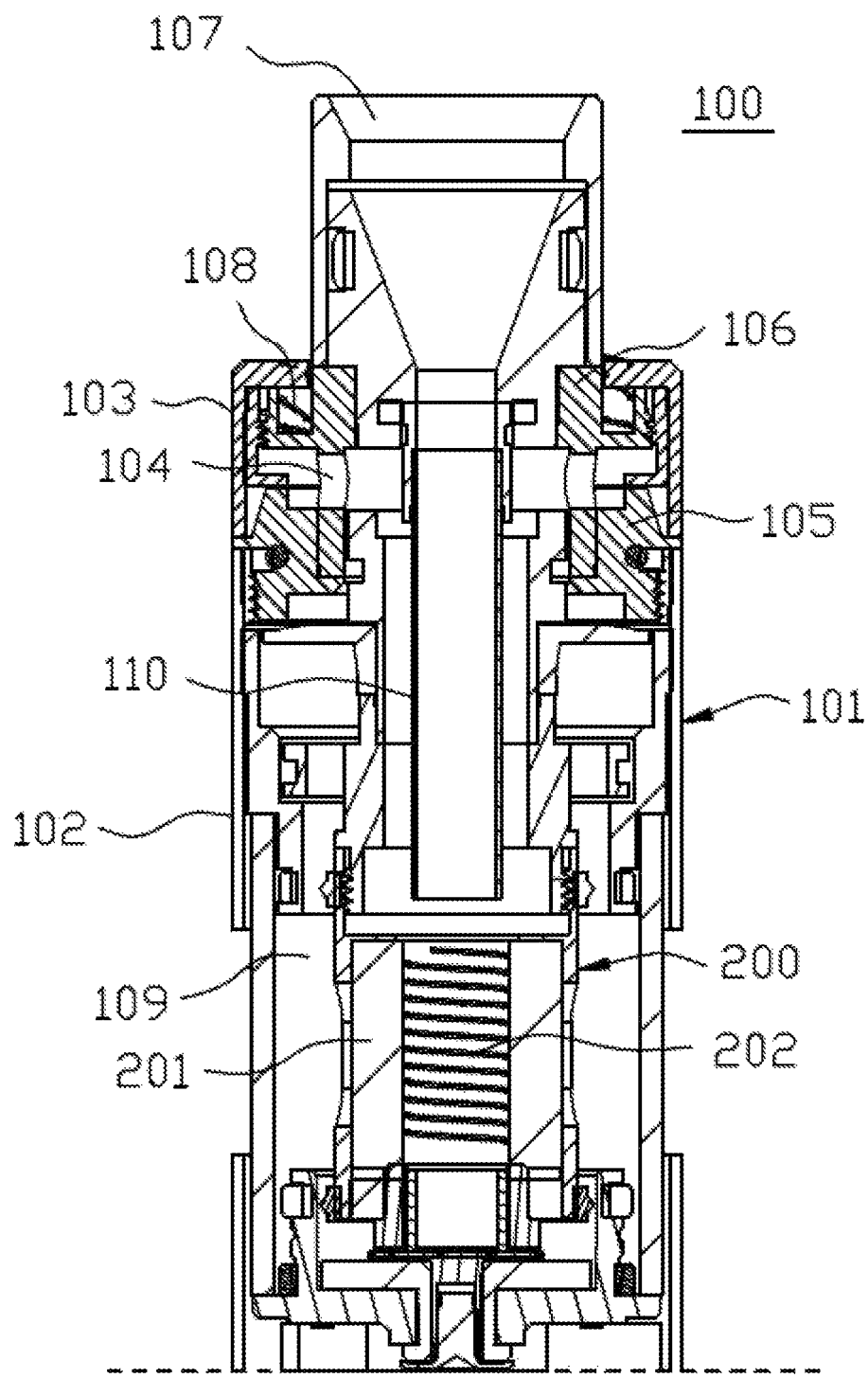
FIG. 1 is a cross-sectional view of the atomizer with adjustable air inlet quantity when the air inlet is closed according to embodiments of the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Referring to FIG. 1, the present disclosure relates to an atomizer 100 with adjusting air inlet quantity, including an atomizer body 101, an aerosol generator 200 and an adjusting cover 103 configured for adjusting air inlet quantity, a liquid storage chamber 109 formed inside the atomizer body 101 and configured for storing tobacco liquid. The aerosol generator 200 is configured for heating the tobacco liquid to generate an aerosol.

At least an air inlet 104 are opened on the atomizer body 101, an air pipe 110 is disposed inside of the atomizer body 101; the air inlet 104 is in communication with the air pipe 110. The air pipe 100 is configured for conducting the aerosol to flow therein. A mouth piece 107 is carried on top of the atomizer body 101. The user may suck the aerosol out from the mouth piece 107. The above air inlet 104 is disposed on an end of the atomizer body close to the mouth piece 107.

The above adjusting cover 103 is connected with the atomizer body 101 by a thread to conceal the air inlet 104. The adjusting cover 103 is configured for being rotated to move up and down along axial direction of the atomizer body 101, to adjust a clearance between an edge 1031 of the adjusting cover 103 and the atomizer body 101, so as to reach a purpose of adjusting air inlet quantity of the air inlet 104. In a state as shown in FIG. 1, the edge 1031 of the adjusting cover 103 tightly abuts the atomizer body 101, with consequently no clearance, exterior airstream fails to flow into the atomizer 100 through the air inlet 104.

More specifically, the atomizer body 101 includes a shell 102, a end cover connected with the shell 102 and a base 106 connected with the end cover 105. The adjusting cover 103 is sleeved on the base 106 and connected with the base 106 by a thread. An outer surface of the adjusting cover 103 is in align with an outer surface of the shell 102 to form an entire surface, which is in favor of artistic appearance of the atomizer 100. Meanwhile, in the embodiment, the air inlet 104 is opened on the base 106 and concealed inside the adjusting cover 103. If there are more than one air inlet 104, multiple air inlets 104 are evenly spaced on side wall of the base 106 to make air more evenly flowing. To be understand, in some embodiments, the above air inlet 104 is disposed on the end cover 105. Based on the users' habits, in some embodiments, the above air inlet 104 and the adjusting cover 103 are also disposed on a lower end of the atomizer body 101.

The above aerosol generator 200 is detachably mounted inside the liquid storage chamber 109, the aerosol generator 200 includes a liquid conductor 201 absorbing tobacco liquid from the liquid storage chamber 109, and a heating element 202. The liquid conductor 201 encircles the heating element 202 to provide tobacco liquid to the heating element 202 for heating.

Figure 2:
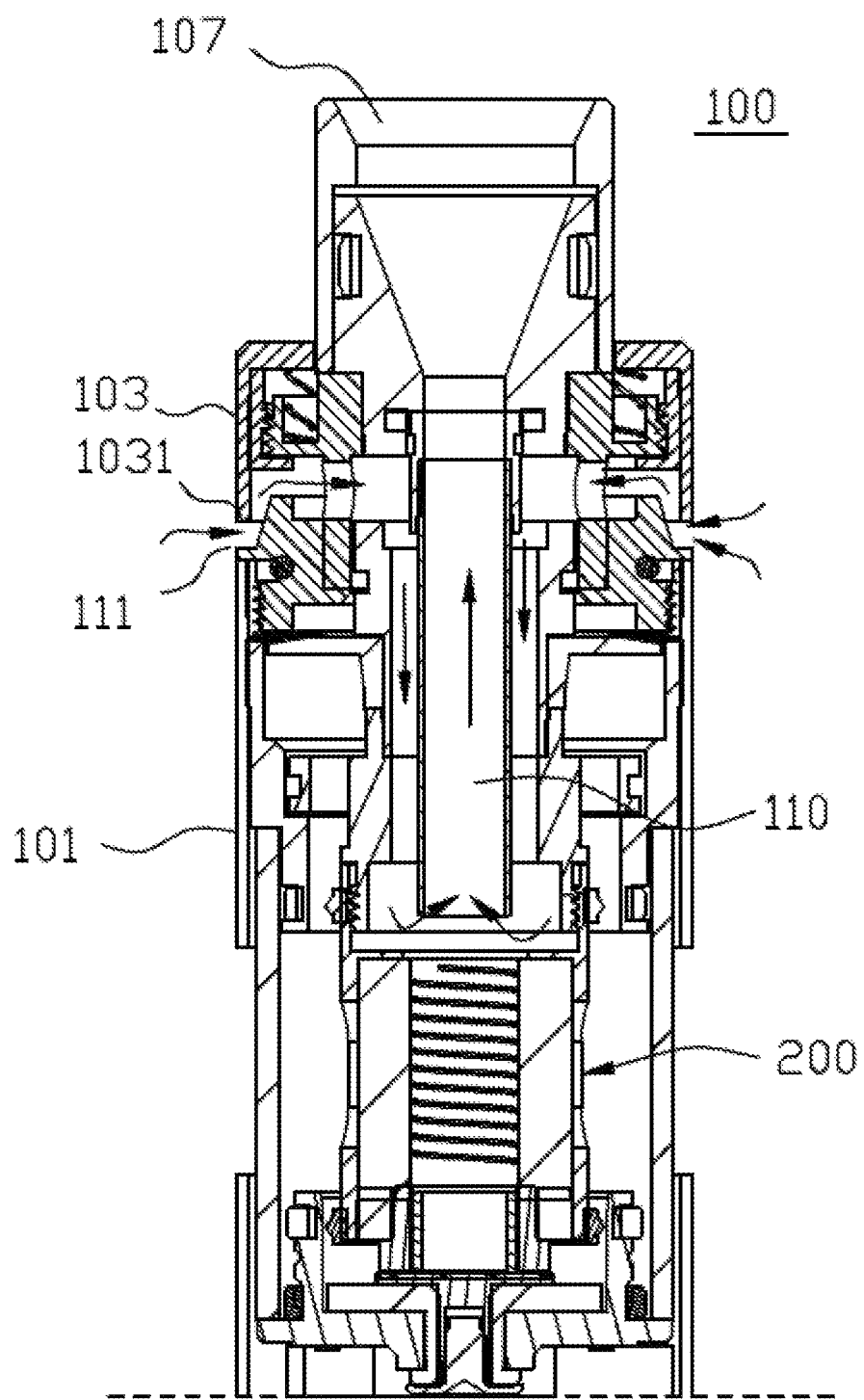
FIG. 2 is a cross-sectional view of the atomizer with adjustable air inlet quantity when the air inlet is opened according to embodiments of the present disclosure.

With reference to FIG. 2, when the user is in a state of smoking, the user may rotate the adjusting cover 103 to move up, a circular clearance 111 is formed between the atomizer body 101 and the edge 1031 of the atomizer cover 103. The size of the clearance 111 is bigger, the air inlet quantity of the air inlet 104 is greater, which the users may adjust by themselves to satisfy their own flavors. When the exterior airstream flows into the air pipe 110 through the air inlet 104, the air pipe 110 is disposed between the aerosol generator 200 and the mouth piece 107, the aerosol generated by the aerosol generator 200 may flow into the mouth piece 107 along with the airstream. The air pipe 110 includes an inflow pipe and an outflow pipe, of which directions of air flowing are opposite to each other, the inflow pipe circles the outflow pipe, when the airstream from the inflow pipe flows downwards to the top of the aerosol generator 200, then carries the aerosol to flow back upwards, finally to be sucked from the mouth piece 107.

Figure 3:
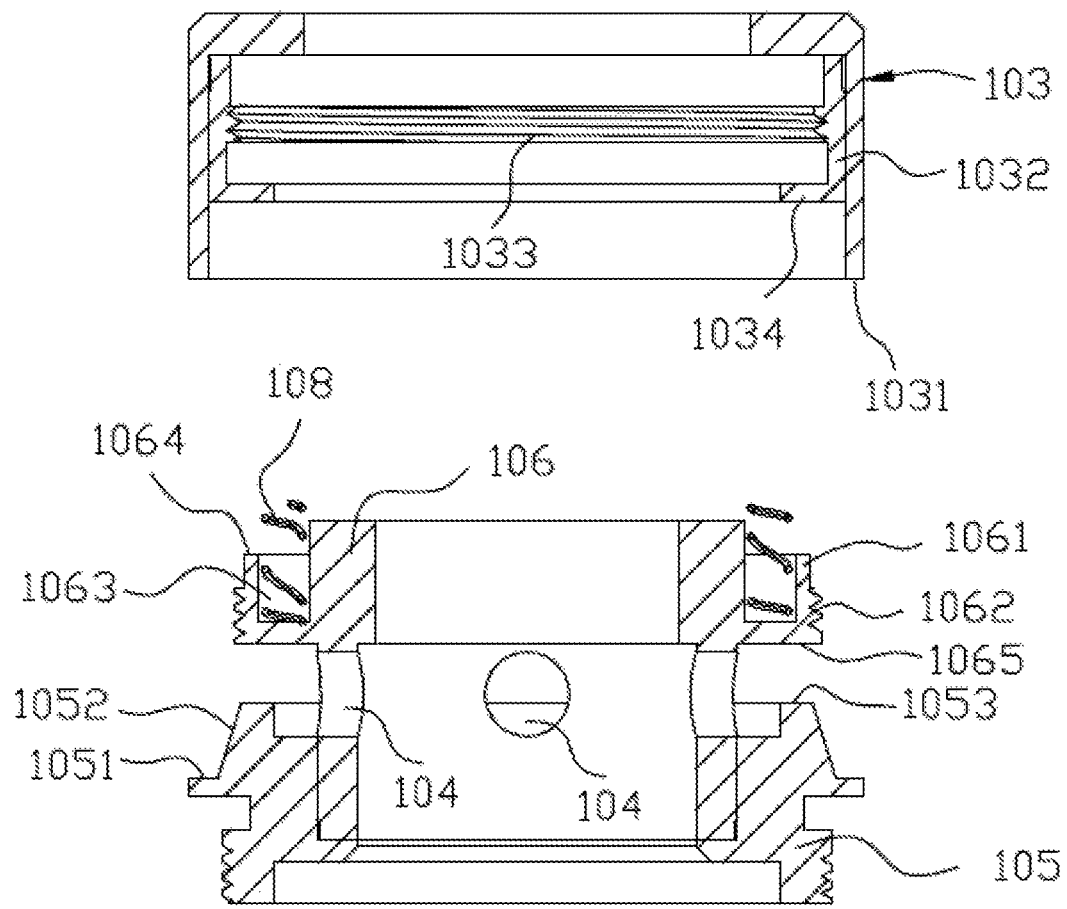
FIG. 3 is a cross-sectional view of the adjusting cover, a end cover and the base connected according to embodiments of the present disclosure.

With reference to FIG. 3, the end cover 105 has a circular stair 1051, the edge 1031 of the adjusting cover 103 abuts against the circular stair 1051, when the adjusting cover 103 is moving up and down, between the edge 1031 of the adjusting cover 103 and the stair 1051 defines a clearance that allows air to flow into the air inlet 104. In some embodiments, the end cover 105 has a cylindrical surface 1052, between the cylindrical surface 1052 and an inside wall of the adjusting cover 103 defines a wedge-shaped air pipe in favor of smooth of air flowing.

The base 106 has a flange 1061, the adjusting cover 103 includes an ancillary component 1032 with a L-shaped section, connected with the flange 1061 by a thread, an inside lateral wall of the ancillary component 1032 has a thread 1033, an outside lateral wall of the flange 1061 has a matched thread 1062 matched with the thread 1033. The ancillary component 1032 includes a limit tongue 1034, confined between a bottom surface of the flange 1061 and a top 1053 of the end cover 105, to limit the adjusting range of the adjusting cover 103.

In some embodiments, to improve the touch feeling, a top surface 1064 of the flange 1061 defines a mounting hole 1063, an elastic element 108 is disposed inside the mounting hole 1063, configured for abutting against top of inner surface of the adjusting cover 103. The elastic element 108 may be an elastic pin, also made by a spring and steel balls. The elastic element 108 is capable of applying a force to the adjusting cover 103, without a certain strength to prevent the adjusting cover 103 from rotating.

Figure 4:
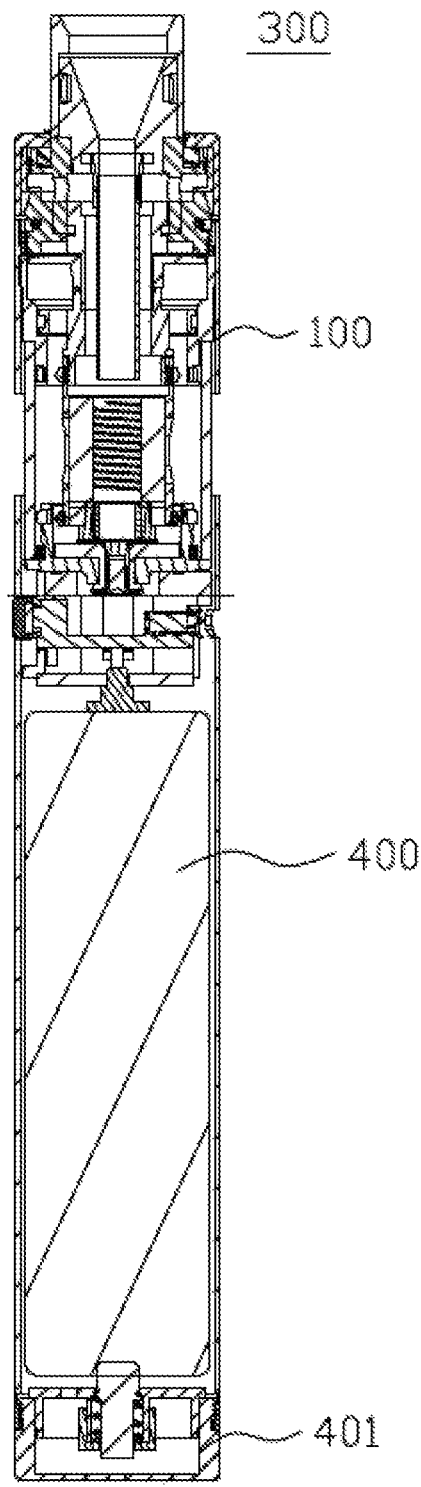
FIG. 4 is a cross-sectional view of an electronic cigarette according to embodiments of the present disclosure.

With reference to FIG. 4, according to embodiments of the present disclosure, an electronic cigarette 300 is further disclosed, including the atomizer 100 with adjustable air inlet quantity and a power supply 400, the atomizer 100 and the power supply 400 may be disposed in one same housing, or connected as two separate parts. In the embodiment, the atomizer 100 and the power supply 400 are disposed in one same housing; one end of the housing has a electric conducting cover 401 detachable to change the power supply 400. The power supply 400 is configured for supplying power to the heating element 202 inside the aerosol generator 200.

Figure 5:
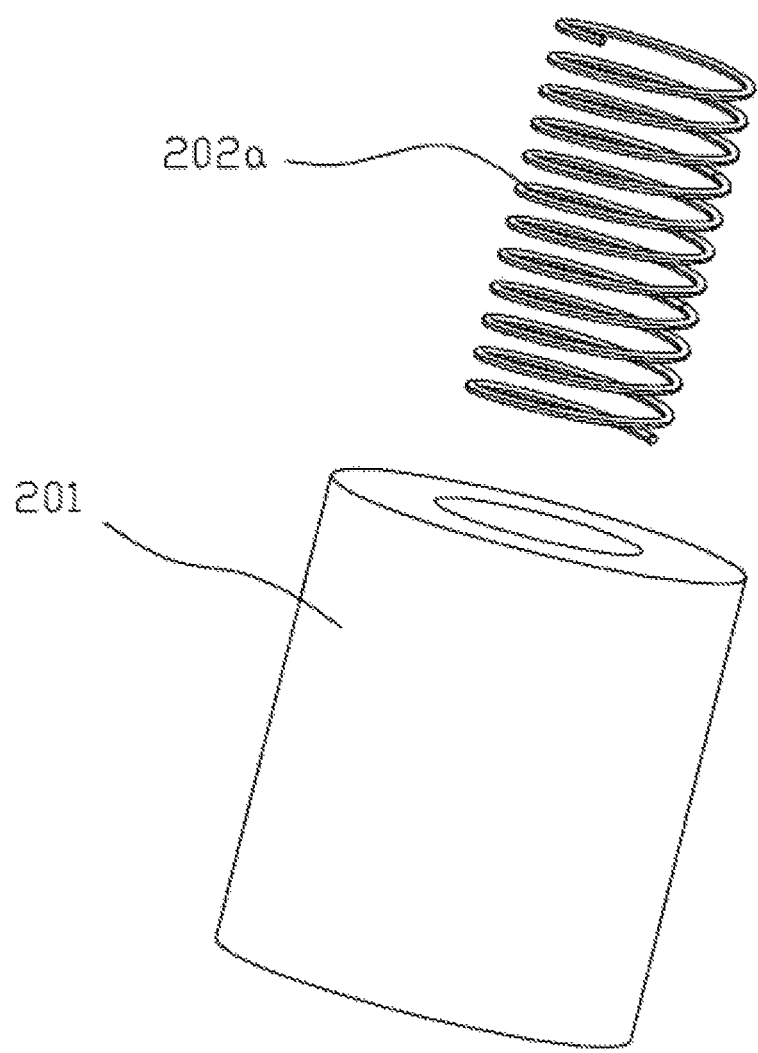
FIG. 5 is a perspective view of a heating element adapting a spiral heating wire according to embodiments of the present disclosure.
Figure 6:
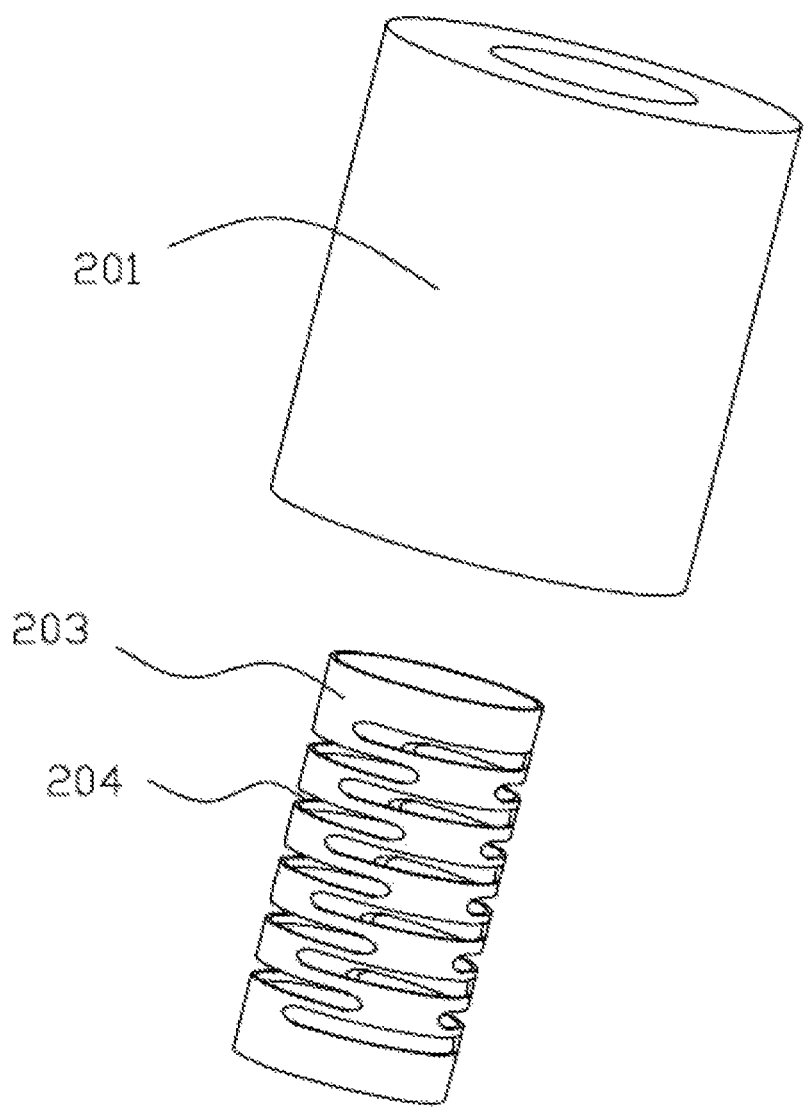
FIG. 6 is a perspective view of the heating element adapting a heating tube according to embodiments of the present disclosure.

With reference to FIG. 5 and FIG. 6, the heating element 202 is a spiral heating wire 202a or a heating tube 203 with several pierced holes 204 opened on a wall of the heating tube 203. The pierced holes 204 are in favor of expelling the aerosol. The liquid conductor 201 encircles the spiral heating wire 202a or the heating tube 203 that are made hollow. The liquid conductor 201 may be the fiber cotton, fiber glass, porous polymer foam material and micro-porous ceramic etc. The heating element 202 and the liquid conductor 201 are made integral as one, for example, sintering the heating tube 203 with inner wall of the micro-porous ceramic together.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is to be claimed is:

1. An atomizer with adjustable air intake quantity, comprising:
   an atomizer body, having a liquid storage chamber formed therein for storing tobacco liquid;
   an aerosol generator configured for aerosolizing the tobacco liquid from the liquid storage chamber to generate an aerosol;
   at least one air inlet formed on the atomizer body;
      an air pipe disposed inside of the atomizer body and configured for conducting the aerosol to flow along the air pipe, the air inlet being in communication with the air pipe; and
   an adjusting cover connected with the atomizer body by a thread to cover the air inlet, the adjusting cover configured for being rotated to move up and down along an axial direction of the atomizer body, to adjust a clearance between an edge of the adjusting cover and the atomizer body;
   wherein the atomizer body comprises an end cover disposed on one end thereof, and a base connected with the end cover, wherein the adjusting cover is sleeved on the base and connected with the base by a thread;
   wherein the end cover comprises a circular stair and the edge of the adjusting cover abuts against the circular stair; a clearance is defined between the edge of the adjusting cover and the stair for allowing air to flow into the air inlet;
   wherein the end cover comprises a cylindrical surface, wherein a wedge-shaped air pipe is defined between the cylindrical surface and an inside wall of the adjusting cover.

2. The atomizer according to claim 1, wherein at least one air inlet is opened on a lateral wall of the base or the end cover.

3. The atomizer according to claim 1, wherein the base comprises a flange, the adjusting cover comprises an ancillary component with an L-shaped section connected with the flange by a thread, and the ancillary component comprises a limit tongue confined between a bottom surface of the flange and a top of the end cover.

4. The atomizer according to claim 3, wherein a top surface of the flange defines a mounting hole, and wherein an elastic element is disposed inside the mounting hole configured for abutting against top of inner surface of the adjusting cover.

5. An electronic cigarette comprising:
   an atomizer with adjustable air intake quantity, comprising:
      an atomizer body, having a liquid storage chamber formed therein for storing tobacco liquid;
      an aerosol generator configured for aerosolizing the tobacco liquid from the liquid storage chamber to generate an aerosol;
      at least one air inlet formed on the atomizer body;
   an air pipe disposed inside of the atomizer body and configured for conducting the aerosol to flow along the air pipe, the air inlet being in communication with the air pipe; and
      an adjusting cover connected with the atomizer body by a thread to cover the air inlet, the adjusting cover configured for being rotated to move up and down along an axial direction of the atomizer body, to adjust a clearance between an edge of the adjusting cover and the atomizer body;
   wherein the electronic cigarette further comprises a power supply;
   wherein the aerosol generator comprises a heating element, the power supply is configured for supplying power to the heating element;
   wherein the atomizer body comprises an end cover disposed on one end thereof, and a base connected with the end cover, wherein the adjusting cover is sleeved on the base and connected with the base by a thread;
   wherein the end cover comprises a circular stair and the edge of the adjusting cover abuts against the circular stair; a clearance is defined between the edge of the adjusting cover and the stair for allowing air to flow into the air inlet;
   wherein the end cover comprises a cylindrical surface, wherein a wedge-shaped air pipe is defined between the cylindrical surface and an inside wall of the adjusting cover.

6. The electronic cigarette according to claim 5, wherein at least one air inlet is opened on a lateral wall of the base or the end cover.

7. The electronic cigarette according to claim 5, wherein the base comprises a flange, the adjusting cover comprises an ancillary component with an L-shaped section connected with the flange by a thread, and the ancillary component comprises a limit tongue confined between a bottom surface of the flange and a top of the end cover.

8. The electronic cigarette according to claim 7, wherein a top surface of the flange defines a mounting hole, and wherein an elastic element is disposed inside the mounting hole configured for abutting against top of inner surface of the adjusting cover.

9. The electronic cigarette according to claim 5, wherein the heating element is a spiral heating wire or a heating tube with pierced holes opened on a wall of the heating tube.

10. The electronic cigarette according to claim 9, wherein the aerosol generator comprises a liquid conductor configured for absorbing tobacco liquid from the liquid storage chamber and providing tobacco liquid to the heating element for heating.

11. The electronic cigarette according to claim 10, wherein the liquid conductor is made of any one of fiber cottons, fiber glasses, porous polymer foam materials and micro-porous ceramic.

* * * * *